United States Patent [19]
Barnitz et al.

[11] Patent Number: 5,810,766
[45] Date of Patent: Sep. 22, 1998

[54] INFUSION/ASPIRATION APPARATUS WITH REMOVABLE CASSETTE

[75] Inventors: James C. Barnitz, Schwenksville; David C. Downey, Holland; Perry Sepielli, Richboro, all of Pa.

[73] Assignee: Chiron Vision Corporation, Claremont, Calif.

[21] Appl. No.: 395,571

[22] Filed: Feb. 28, 1995

[51] Int. Cl.⁶ .................................................. A61M 1/00
[52] U.S. Cl. ............................................. 604/34; 604/317
[58] Field of Search ................................. 604/317, 319, 604/31, 34, 35

[56] References Cited

U.S. PATENT DOCUMENTS

| | | |
|---|---|---|
| Re. 33,250 | 7/1990 | Cook . |
| 3,360,185 | 12/1967 | Woolridge . |
| 3,589,363 | 6/1971 | Banko et al. . |
| 3,599,639 | 8/1971 | Spotz . |
| 3,693,613 | 9/1972 | Kelman . |
| 3,723,030 | 3/1973 | Gelfand . |
| 3,841,799 | 10/1974 | Spinosa et al. . |
| 3,920,014 | 11/1975 | Banko . |
| 4,024,866 | 5/1977 | Wallach . |
| 4,144,644 | 3/1979 | Olsen . |
| 4,168,707 | 9/1979 | Douvas et al. . |
| 4,168,943 | 9/1979 | Banko . |
| 4,180,074 | 12/1979 | Murry et al. . |
| 4,184,510 | 1/1980 | Murry et al. . |
| 4,187,057 | 2/1980 | Xanthopoulos . |
| 4,226,590 | 10/1980 | Hofmann . |
| 4,236,880 | 12/1980 | Archibald . |
| 4,256,437 | 3/1981 | Brown . |
| 4,256,442 | 3/1981 | Lamadrid et al. . |
| 4,324,243 | 4/1982 | Helfgott et al. . |
| 4,395,258 | 7/1983 | Wang et al. . |
| 4,424,011 | 1/1984 | O'Brien et al. . |
| 4,445,826 | 5/1984 | Tarr . |
| 4,464,172 | 8/1984 | Lichtenstein . |
| 4,468,219 | 8/1984 | George et al. . |
| 4,475,904 | 10/1984 | Wang . |
| 4,479,760 | 10/1984 | Bilstad et al. . |
| 4,482,347 | 11/1984 | Borsanyi . |
| 4,493,695 | 1/1985 | Cook . |
| 4,493,698 | 1/1985 | Wang et al. . |
| 4,515,589 | 5/1985 | Austin et al. . |
| 4,526,515 | 7/1985 | DeVries . |

(List continued on next page.)

FOREIGN PATENT DOCUMENTS

| | | |
|---|---|---|
| 0040181 | 11/1981 | European Pat. Off. . |
| 2176717 | 1/1987 | United Kingdom . |
| WO8607249 | 12/1986 | WIPO . |

OTHER PUBLICATIONS

"Understanding Peristaltic, Diaphragm, and Venturi Systems," believed to describe pumps in use prior to the filing date of the present application.

Search report dated Jan. 26, 1996, PCT application No. PCT/US95/13592, filed Oct. 27, 1995.

U.S. application Ser. No. 08/395,583, filed Feb. 28, 1995 (PD–4368).

U.S. application Ser. No. 08/330,920, filed Oct. 28, 1994 (PD–4369).

*Primary Examiner*—Michael A. Brown
*Attorney, Agent, or Firm*—Pillsbury Madison & Sutro LLP

[57] ABSTRACT

An infusion/aspiration apparatus including a base member and first and second cassettes including a base member and first and second cassettes releasably connected to a base member. The first cassette forms an aspiration passageway and a collection area, and the second cassette includes a body and an infusion tube. Preferably, the base member and the second cassette form a vacuum passageway in fluid communication with the aspiration passageway. In operation, an aspiration tube is connected to an inlet of the aspiration passageway, and an outlet of the vacuum passageway is connected to a source of vacuum pressure. An infusion fluid is conducted through the infusion tube and to a surgical site, and that site is aspirated via the aspiration tube. The aspirated materials are drawn into the aspiration passageway and thence into the collection area.

30 Claims, 4 Drawing Sheets

U.S. PATENT DOCUMENTS

| | | | |
|---|---|---|---|
| 4,537,561 | 8/1985 | Xanthopoulos . | |
| 4,599,055 | 7/1986 | Dykstra . | |
| 4,626,248 | 12/1986 | Scheller | 604/319 |
| 4,627,833 | 12/1986 | Cook . | |
| 4,643,717 | 2/1987 | Cook et al. . | |
| 4,650,469 | 3/1987 | Berg et al. . | |
| 4,664,601 | 5/1987 | Uchida et al. . | |
| 4,670,006 | 6/1987 | Sinnett et al. . | |
| 4,685,902 | 8/1987 | Edwards et al. . | |
| 4,706,687 | 11/1987 | Rogers . | |
| 4,710,163 | 12/1987 | Butterfield . | |
| 4,713,051 | 12/1987 | Steppe et al. | 604/35 X |
| 4,714,464 | 12/1987 | Newton . | |
| 4,735,558 | 4/1988 | Kienholz et al. . | |
| 4,740,202 | 4/1988 | Stacey et al. . | |
| 4,757,814 | 7/1988 | Wang et al. . | |
| 4,758,238 | 7/1988 | Sunblom et al. . | |
| 4,759,349 | 7/1988 | Betz et al. . | |
| 4,770,187 | 9/1988 | Lash et al. . | |
| 4,770,654 | 9/1988 | Rogers et al. . | |
| 4,773,897 | 9/1988 | Scheller et al. . | |
| 4,790,816 | 12/1988 | Sunblom et al. . | |
| 4,798,580 | 1/1989 | DeMeo et al. | 604/34 X |
| 4,810,242 | 3/1989 | Sunblom et al. . | |
| 4,820,265 | 4/1989 | DeSatnick et al. . | |
| 4,838,281 | 6/1989 | Rogers et al. . | |
| 4,838,865 | 6/1989 | Flank et al. . | |
| 4,898,579 | 2/1990 | Groshong et al. . | |
| 4,900,302 | 2/1990 | Newton . | |
| 4,902,276 | 2/1990 | Zakko . | |
| 4,904,168 | 2/1990 | Cavoto et al. . | |
| 4,933,843 | 6/1990 | Scheller et al. . | |
| 4,988,336 | 1/1991 | Kohn . | |
| 5,087,245 | 2/1992 | Doan . | |
| 5,106,366 | 4/1992 | Steppe | 604/35 X |
| 5,125,891 | 6/1992 | Hossain et al. . | |
| 5,163,900 | 11/1992 | Wortrich . | |
| 5,242,404 | 9/1993 | Conley et al. . | |
| 5,249,121 | 9/1993 | Baum et al. . | |
| 5,267,956 | 12/1993 | Beuchat . | |
| 5,328,478 | 7/1994 | McVay . | |
| 5,346,470 | 9/1994 | Hobbs et al. . | |
| 5,368,559 | 11/1994 | Kusmierczyk et al. . | |
| 5,376,070 | 12/1994 | Purvis et al. | 604/31 |
| 5,380,280 | 1/1995 | Peterson . | |
| 5,470,312 | 11/1995 | Zanger et al. . | |
| 5,484,428 | 1/1996 | Drainville | 604/319 |

INFUSION/ASPIRATION APPARATUS WITH REMOVABLE CASSETTE

BACKGROUND OF THE INVENTION

This invention generally related to surgical apparatus, and more specifically, to apparatus for providing aspiration and infusion during surgery. Even more specifically, the present invention relates to such apparatus that is particularly well suited for use in ophthalmic microsurgical systems.

Microsurgical procedures are gaining an ever-increasing acceptance in the surgical community for preforming precise, minimum invasive surgery for various parts of the body, and one particularly widespread microsurgical application is in the field of ophthalmology. In this application, commonly, a handpiece having a small tool is used either to cut or mascerate the eye tissue while an irrigation or infusion liquid is brought to the surgery site. The cut or mascerated tissue is carried away from the surgical site by a suction conduit or tube to a collection vessel such as a bag or bottle. The surgical site may be illuminated by light conducted to that site through an optical fiber.

Consoles are specifically designed for these ophthalmic procedures. These consoles are used to operate the tools and the suction and infusion lines used in the procedures, and to generate the light that is used to illuminate the surgical sites. Typically, these consoles have a modular design and include a multitude of separable or removable modules, with each module being used to operate or to perform a specific task. For example, one specific module may be used to infuse and aspirate the surgical site.

With one prior art console, the irrigation and aspiration fluids are conducted through a removable cassette that is the only part of the console that comes into direct contact with these fluids. This cassette is designed to be used only once and then to be replaced after that one use. Occasionally, this cassette is improperly reused, normally to save the cost of replacing the cassette.

SUMMARY OF THE INVENTION

An object of this invention is to improve infusion/aspiration modules used in surgical procedures.

Another object of the present invention is to provide a very inexpensive, removable cassette for an infusion/aspiration module.

A further object of this invention is to provide a low procedural cost cassette, for use in a surgical system, while maintaining ease of use by having the cassette comprise a main unit, which is intended to be used for several procedures, and a sub-unit, which is intended to be replaced for every procedure.

These and other objectives are attained with an infusion/aspiration apparatus comprising a base member and first and second cassettes releasably connected to the base member. The first cassette forms an aspiration passageway for receiving liquids and materials from a surgical site, and a collection area in fluid communication with the aspiration passageway for receiving and collecting said liquids and materials. The second cassette includes a body and an infusion tube connected to and supported by the body for conducting an infusion fluid. Preferably, the base member and the second cassette form a vacuum passageway in fluid communication with the aspiration passageway.

In operation, an aspiration tube is connected to an inlet of the aspiration passageway, and an outlet of the vacuum passageway is connected to a source of vacuum pressure. An infusion fluid is conducted through the infusion tube and to the surgical site, and that site is aspirated via the aspiration tube. The aspirated materials are drawn through the aspiration tube, into the aspiration passageway and thence into the collection area. During this operation, occlusion means may be used to control the flow of the infusion fluid through the infusion tube.

The second cassette, which may be very inexpensive, is designed to be replaced after each use. The first cassette, which never comes into contact with the infusion fluid prior to being conducted to the surgical site, is designed to be used for a multitude of procedures. This first cassette may be provided with a drain opening to allow aspirated materials to be drained from the first cassette while that cassette is mounted on the infusion/aspiration apparatus.

Further benefits and advantages of the invention will become apparent from a consideration of the following detailed description given with reference to the accompanying drawings, which specify and show preferred embodiments of the invention.

DETAILED DESCRIPTION OF THE PREFERRED EMBODIMENTS

FIGS. 1–6 illustrate infusion/aspiration apparatus 10 generally comprising base member 12, first cassette 14, second cassette 16, first holding means 20, second holding means 22 and occlusion means 24. First cassette 14 forms aspiration passageway 26 and fluid collection area 30, and second cassette includes body 32 and infusion tube 34. Also, preferably, base member 12 and second cassette 16 form vacuum passageway 36.

Figure 1:
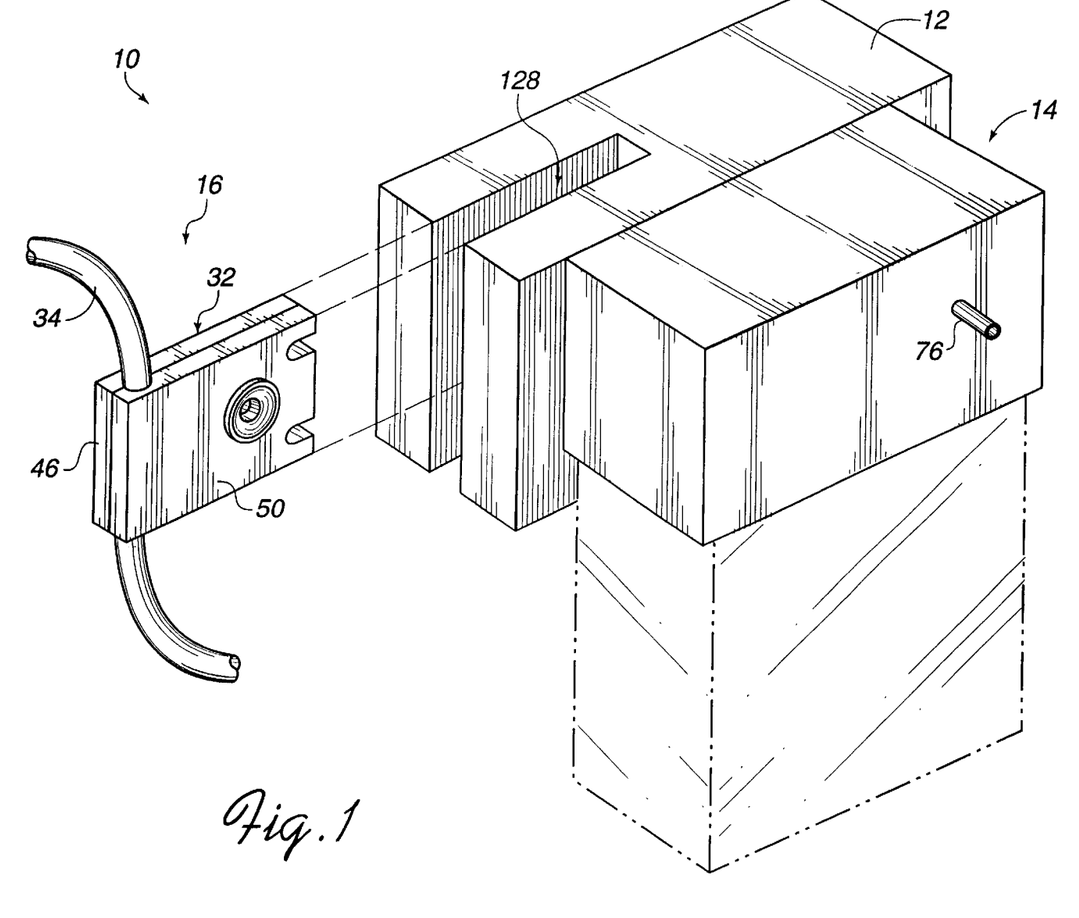
FIG. 1 is an orthogonal view of an infusion/aspiration apparatus embodying the present invention.

Preferably, first cassette includes shell or body 38, T-tube 40, end cap 42 and check valve 44, and body 32 of second cassette 16 includes first and second cassette sections 46 and 50 and filter 52. In addition, first holding means 20 includes pivot subassembly 54 and latch subassembly 56, and second holding means 22 includes first and second resilient members 60 and 64 and reciprocating means 66. Also occlusion means 24 includes pincher 70, pincher block 72 and reciprocating means 74. FIG. 1 also shows aspiration connector 76 mounted on first cassette 14.

With the embodiment of apparatus 10 shown in the drawings, pivot sub-assembly 54 includes first and second pins 82 and 84 and first and second hooks 86 and 90; and latch sub-assembly 56 includes opening 92, lever 94 and spring 96. Also, occlusion means 24 includes pincher block 102, pincher 104 and reciprocating means 106. The embodiment of apparatus 10 shown in the drawings further includes second and third occlusion means 110 and 112. This second occlusion means 110 includes pincher block 114, pincher 116 and reciprocating means 120, and third occlusion means 112 includes pincher 122, guide member 124 and reciprocating means 126.

Generally, cassettes 14 and 16 are releasably held on base member 12 by first and second holding means 20 and 22, respectively. Infusion tube 34 is connected to and is supported by cassette body 32 for conducting an infusion fluid from a source thereof (not shown) to a surgical site (also not shown). Aspiration passageway 26 is provided for receiving liquids and materials from the surgical site, and fluid collection area 30 is in communication with the aspiration passageway for receiving and collecting those liquids and materials. In addition, preferably, passageway 36 is in fluid communication with aspiration vacuum passageway 26 to develop a vacuum pressure therein—that is, a pressure low enough to draw fluids and materials into and through the aspiration passageway from the surgical site.

In operation, an aspiration tube is connected to aspiration connector 76, and an outlet of vacuum passageway 36 is connected to a source of vacuum pressure, such as a vacuum pump. An infusion fluid is conducted through tube 34 to the surgical site, and that site is aspirated via the aspiration tube. The aspirated materials are drawn through the aspiration tube, into aspiration passageway 26, and thence into collection area 30. During this operation, occlusion means 24 may be used to control the flow of the infusion fluid through tube 34.

Second cassette 16 is designed to be replaced after each use; and this may be done by disconnecting cassette 16 from base member 12, as more fully discussed below, and then replacing this cassette 16 with an identical cassette. First cassette 14 is designed to be used for a multitude of procedures; and preferably this cassette is provided with a drain opening, and the cassette is drained empty after each use. When it is appropriate to replace cassette 14, this may be done by disconnecting the cassette from base member 12, also as more fully discussed below, and then replacing this cassette 14 with an identical cassette.

Figure 2:
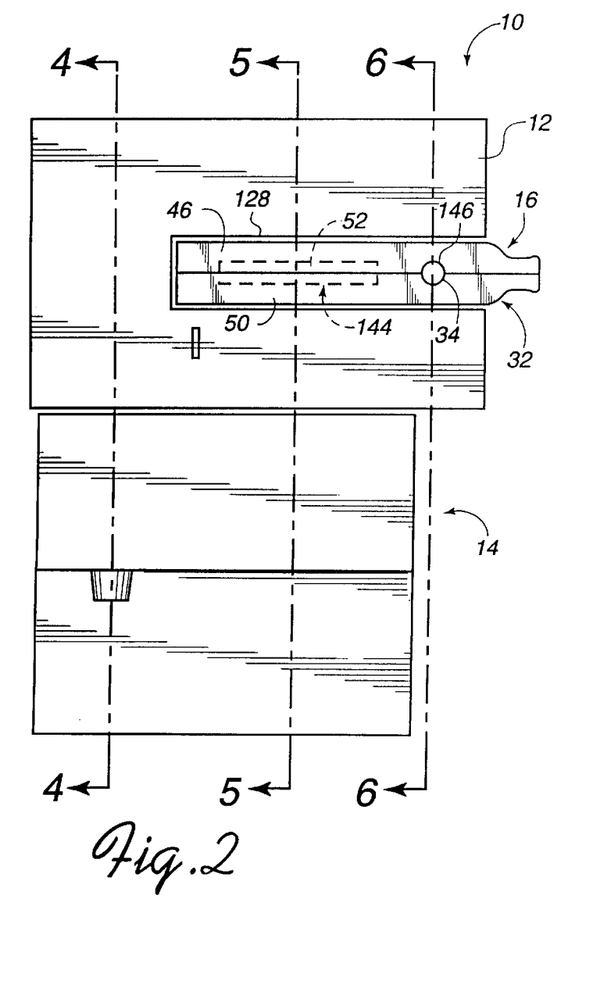
FIG. 2 is a top view of the apparatus of FIG. 1.
Figure 3:
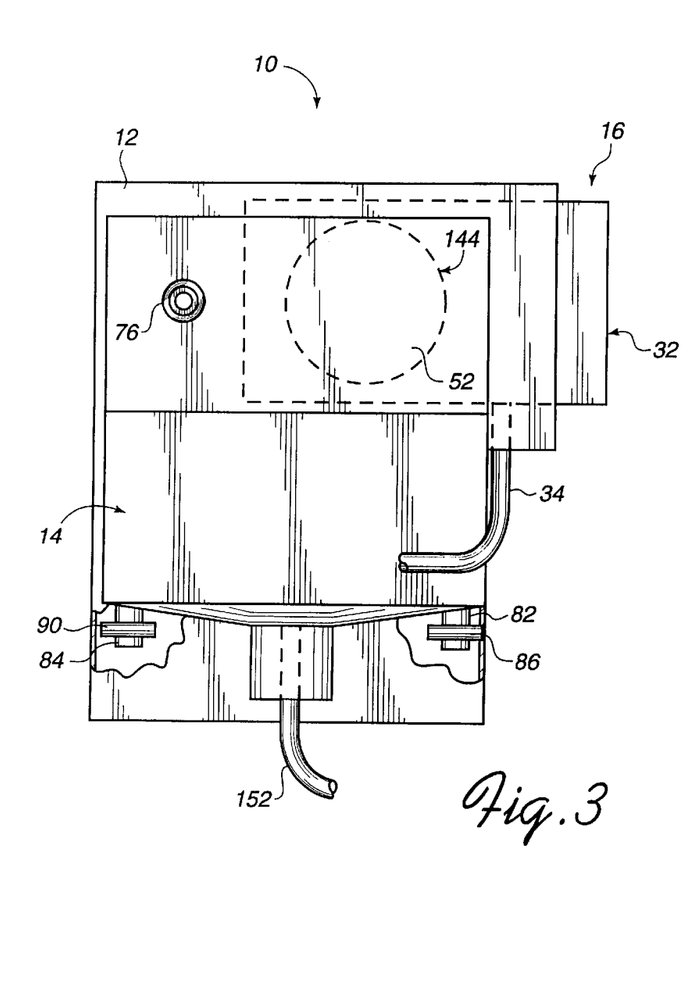
FIG. 3 is a front of the infusion/aspiration apparatus.
Figure 4:
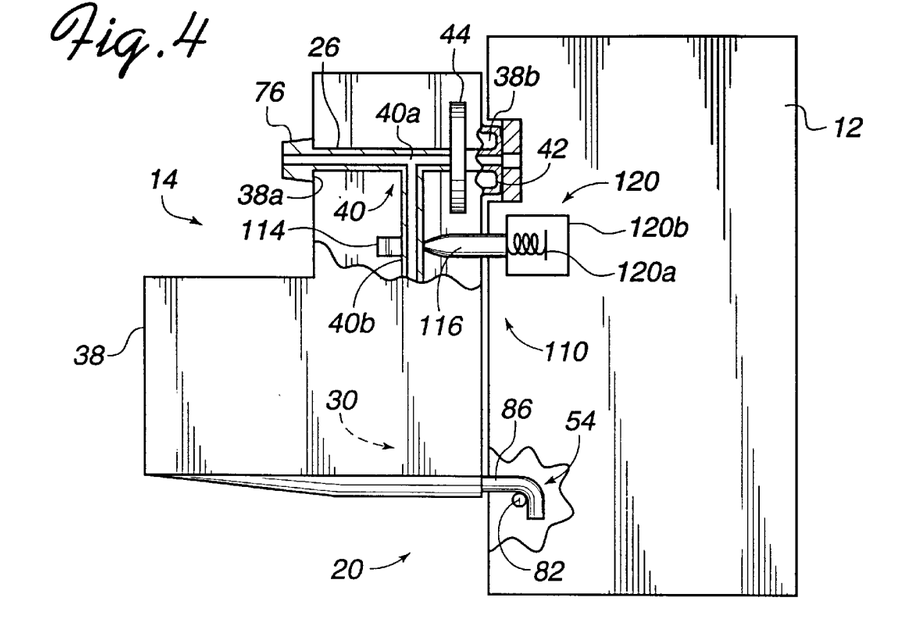
FIG. 4 is a cross-sectional view of the infusion/aspiration apparatus taken, along plane 4—4 of FIG. 2.
Figure 5:
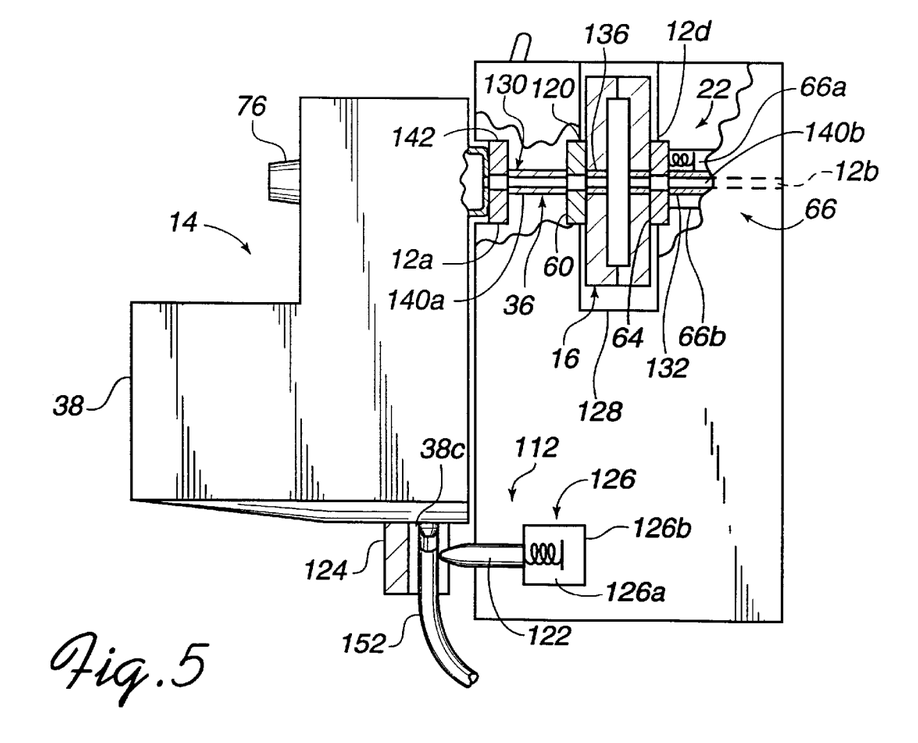
FIG. 5 is another cross-sectional view of the infusion/aspiration apparatus and taken along plane 5—5 of FIG. 2.
Figure 6:
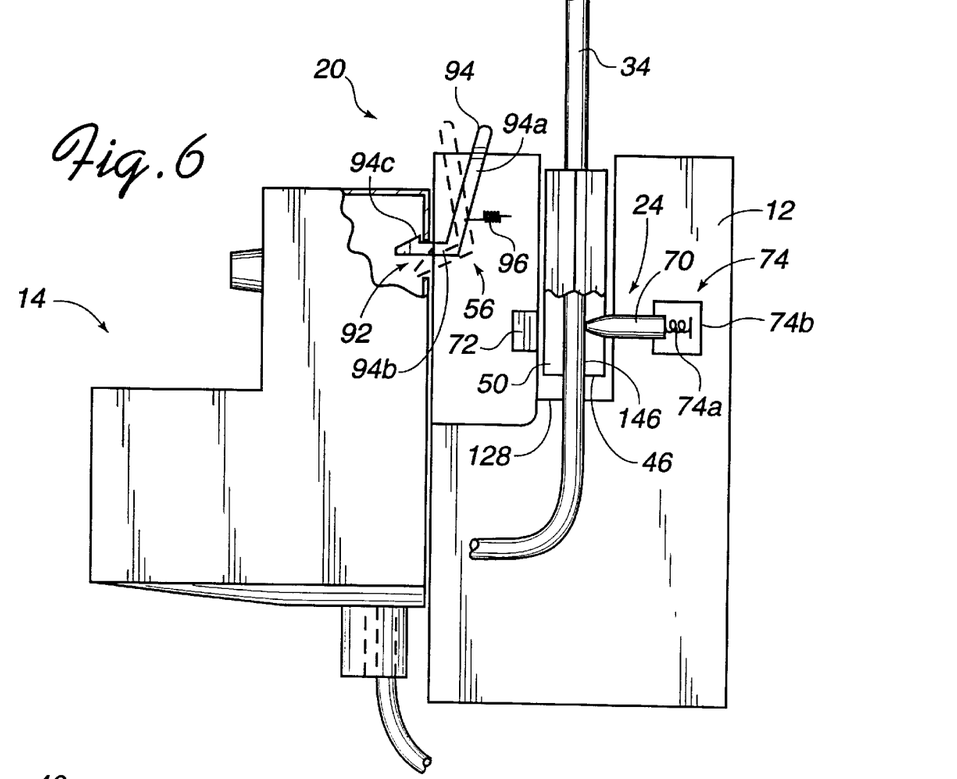
FIG. 6 is third cross-sectional view of the infusion/aspiration apparatus, taken along plane 6—6 of FIG. 2.

With particular reference to FIGS. 2 and 5, base member 12 forms an upper, elongated cassette slot 128 and second cassette 16 is releasably held therein. Also, with this preferred arrangement, base member 12 forms first and second sections 130 and 132 of vacuum passageway 36, and cassette 16 form a third section 136 of that vacuum passageway, located in fluid communication with, and in series between, passageway sections 130 and 132. More specifically, base member 12 defines inlet 12a, outlet 12b and intermediate openings 12c and 12d. Tubular member 140a extends between inlet 12a and opening 12c and forms first section 130 of passageway 36, and tubular member 140b extends between opening 12d and outlet 12b and forms second section 132 of the vacuum passageway. Sealing member 142 may be located between cassette 14 and tubular member 140a to seal the interface between base member 12 and cassette 14, and sealing members 60 and 62 may be located between tubular members 140a and 140b, respectively, and cassette 16 to seal the interfaces therebetween.

Figure 7:
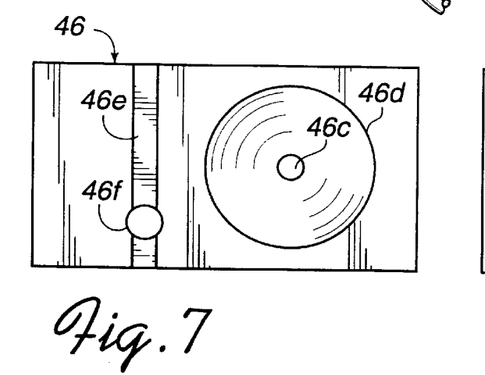
FIG. 7 is a front view of a section of one of the cassettes of the infusion/aspiration apparatus.
Figure 8:
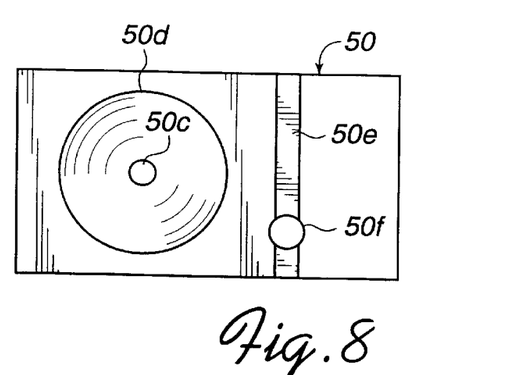
FIG. 8 is a front view of another section of the same cassette of the infusion/aspiration apparatus.

The preferred embodiment of cassette 16 is shown in greater detail in FIGS. 7 and 8; and as illustrated therein, cassette body includes first and second sections 46 and 50 and filter 52. Cassette sections 46 and 50 are substantially mirror images of each other; and each section has the general shape of a thin cube, including generally planar, parallel and rectangular inside and outside faces. Each cassette section forms a central through opening 46c, 50c extending between the inside and outside faces of the cassette section; and the inside face of each cassette section also forms a central circular recess 46d, 50d and a groove 46e, 50e extending from the top to the bottom of the cassette section. Preferably, each cassette section also forms a lateral through opening 46f, 50f that is aligned with a portion of groove 46e, 50e. In use, cassette sections 46 and 50 are held together, with the through openings 46c and 46f central recess 46d and groove 46e of cassette section 46 aligned, respectively, with the through openings, 50c and 50f central recess 50d and groove 50e of cassette section 50. In this way, through openings 46c and 50c form a through conduit extending through cassette body; and, in apparatus 10, this conduit forms section 136 of vacuum passageway 36. In addition, recesses 46d and 50d form internal cavity 144 in cassette body 32, and grooves 46e and 50e from channel 146 extending through the cassette body. In cassette 14, infusion tube 34 extends through channel 146; and preferably tube 34 is securely clamped in channel 146, between cassette sections 46 and 50. Also, filter 52 is located in cavity 144 and preferably the filter substantially or completely fills that cavity. Filter 52 thus extends across vacuum passageway 36, and preferably the filter is a hydrophobic filter and is used to prevent fluids from being transmitted through the vacuum passageway.

Cassette sections 46 and 50 may be made of any suitable materials and may be connected together in any appropriate manner. For example, the cassette sections may be made from a plastic and held together by a suitable adhesive.

As previously mentioned, occlusion means 24 is provided to control the flow of fluid through infusion tube 34, and preferably this occlusion means includes pincher 70, pincher block 72 and reciprocating means 74. More specifically, pincher block 72 is mounted on base member 12 and extends into opening 46f of cassette 16, to a position adjacent infusion tube 34. Pincher 70 is supported on base member 12 for reciprocating movement into opening 50f, and reciprocating means 74 is connected to pincher 70 to reciprocate the pincher into engagement with infusion tube 34 to pinch that tube between the pincher and pincher block 72, and thereby control or prevent fluid flow through the infusion tube.

Any suitable means may be used to support pincher 70 for the desired reciprocating movement, and any appropriate means may be used to reciprocate the pincher. For example, reciprocating means 74 may include a spring 74a and an electrically actuated solenoid 74b. Spring 74a engages pincher 70 and urges the pincher away from infusion tube 34. Solenoid 74b is connected to pincher 70 and, when actuated, forces the pincher against infusion tube 34, to the left as viewed in FIG. 6, against the force of spring 74a, to pinch the infusion tube between the pincher and pincher block 72.

In addition, any suitable means may be used to releasably hold cassette 16 on base member 12; and with reference to FIG. 5, preferably this holding means includes the above-discussed sealing members 60 and 64 and reciprocating means 66. More specifically, cassette 16 is located between sealing members 60 and 64, which are mounted on base member 12, on opposite sides of this cassette. Also, sealing member 64 is supported by base member 12 for reciprocating movement, to the left and to the right as viewed in FIG. 5, and reciprocating means 66 is provided to reciprocate sealing member 64. To remove cassette 16 from apparatus 10, reciprocating means 66 is actuated to move sealing member 64 to the right as viewed in FIG. 5, eliminating or reducing the pressure between sealing members 60 and 64 and the cassette. An operator can then remove cassette 16 from apparatus 10 by simply pulling the cassette away from base member 12, and specifically, out of cassette slot 128.

After cassette 16 has been removed, a replacement cassette can be inserted into apparatus 10 by simply inserting the replacement cassette into slot 128, between sealing members 60 and 64 and then reciprocating means 66 can be used to move sealing member 64 to the left as viewed in FIG. 5, securely clamping the replacement cassette between sealing members 60 and 64.

Any suitable arrangement may be used to support sealing member 64 for the desired reciprocating movement. For instance, sealing member 64 may be mounted on a sleeve, which in turn is supported for limited axial sliding movement. Likewise, any suitable means may be used to reciprocate sealing member 64, and for example reciprocating means 66 may include an electrically actuated solenoid 66a and spring 66b. Spring 66b engages sealing member 64, and urges the sealing member into pressure engagement against cassette 16. Solenoid 66a is connected to sealing member 64 and, when actuated, pulls the sealing member to the right, as viewed in FIG. 5, against the force of spring 66b.

With the embodiment of cassette 14 shown in the drawings, the cassette preferably includes an outer shell 38, T-tube 40, end cap 42 and check valve 44. Shell 38 is generally hollow, the bottom, inside portion of the shell forms collection area 30, and the shell forms front, back and bottom openings 38a, 38b and 38c. T-tube 40 has a t-shape, including upper horizontal section 40a, and a vertical section 40b connected and extending downward from section 40a. T-tube section 40a and end cap 42 define aligned conduits that form aspiration passageway 26, and check valve 44 extends through or in that passageway. In particular, a forward end of T-tube 40 extends through front opening 36a, T-tube section 40a extends rearward therefrom, and a back end of T-tube section 40a is connected to check valve 44. End cap 42 is mounted on shell 38, over back opening 38b, the end cap extends forward, through that back opening, and a front end of the end cap is connected to check valve 44. Check valve 44 allows liquid to pass left to right through the check valve while preventing the reverse flow of liquid—that is, from the right to the left through the check valve.

T-tube section 40b extends downward from T-tube section 40a and is in fluid communication with section 40a and liquid collection area 30. As fluids and materials are conducted rearward through T-tube section 40a, those fluids and materials pass downward, via T-tube section 40b, into liquid collection area 30.

Occlusion means 110 is provided to selectively occlude T-tube section 40b to inhibit or prevent the flow of materials therethrough. With the preferred embodiment of occlusion means 110, pincher block 114 is mounted on cassette 14, adjacent tube section 40b; and pincher 116 is reciprocally mounted on base member 12, also adjacent tube section 40b, but opposite the pincher block. Pincher 116 is supported for reciprocating movement, toward and away from tube section 40b; and reciprocating means 120 is connected to pincher 116 to reciprocate the pincher into engagement with tube section 40b to pinch that tube section between pincher 116 and pincher block 114, and thereby control or prevent flow through this tube section.

Any appropriate means may be used to support pincher 116 and pincher block 114, and any suitable means may be used to reciprocate the pincher. Preferably, reciprocating means 120 includes a spring 120a and an electrically actuated solenoid 120b. Spring 120a engages pincher 122, and urges the pincher away from tube section 40b. Solenoid 120b is connected to pincher 122 and, when actuated, forces the pincher against tube section 40b to pinch that tube section between the pincher and pincher block 114.

Preferably, cassette 14, specifically shell 38 thereof, forms a lower opening 38c to drain fluids from liquid collections area 30; and drainage tube 152 is connected to cassette 14, in communication with drain opening 38c, to conduct fluids therefrom to a suitable receptacle. This receptacle may be, for instance, a large waste fluid container.

Occlusion means 112 is provided to selectively occlude drainage tube 152 to inhibit or prevent the flow of liquid therethrough. With the embodiment of occlusion means 112 illustrated in the drawings, guide member 124 is connected to cassette body 38 and extends downward therefrom, closely adjacent drainage tube 152; and pincher 122 is supported by base member 12, also closely adjacent drainage tube 152, and opposite guide member 124. Pincher 122 is also supported for reciprocating movement toward and away from drainage tube 152; and reciprocating means 126 is connected to pincher 122 to reciprocate the pincher into engagement with the drainage tube to pinch that tube between the pincher and guide member 124, and thus prevent liquid flow through drainage tube 152.

Any suitable means may also be employed to support and to reciprocate pincher 122. For instance, reciprocating means 126, like reciprocating means 120, may include a spring 126a and an electrically actuated solenoid 126b. With reciprocating means 126, however, spring 126a engages pincher 122 and forces the pincher to push drainage tube 152 against guide member 124, so that the drainage tube is normally closed and normally liquid does not flow through the tube. Solenoid 126b is connected to pincher 122 and, when actuated, pulls the pincher away from drainage tube 152 against the force of spring 126a, opening the drainage tube and allowing liquid to pass therethrough.

Figure 9:
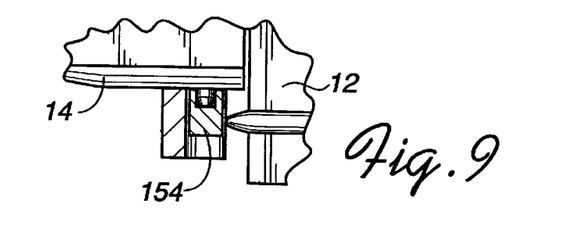
FIG. 9 is a partial side view, partly in cross-section of another cassette of the infusion/aspiration apparatus.

It is not necessary to provide cassette 14 with drain opening 38c and drainage tube 152. FIG. 9 shows an embodiment in which cap 154 is attached to cassette 14 to close the drain opening. Preferably, if cassette 14 is not provided with a drain opening, or that drain opening is closed, then the cassette is used for only one surgical procedure.

As mentioned above, connecting means 20 releasably connects cassette 14 to base member 12, and connecting means 20 preferably includes pivot sub-assembly 54 and latch sub-assembly 56. More particularly, pins 82 and 84 of sub-assembly 54 are connected to and extend outward from base member 12, specifically opposite lateral side thereof, and preferably the axes of pins 82 and 84 are co-linear. Hooks 86 and 90 are mounted on the body of cassette 14 and extend outward therefrom. In apparatus 10, the back ends of hooks 86 and 90 curve rearwardly downwardly, and the back ends of these hooks are mounted on pins 82 and 84, connecting cassette 14 to base member 12 while allowing this cassette to pivot about the axes of these pins.

Latch sub-assembly 56 is provided to selectively hold cassette 14 in place in apparatus 10 or allow cassette 14 to pivot about pins 82 and 84. More specifically, latch sub-assembly 56 has an open position and a closed position. In the open position, latch sub-assembly 56 allows cassette 14 to pivot relative to base member 12, and specifically, about the axes of pins 82 and 84. In the closed position, the latch sub-assembly 56 holds cassette 14 in a tight pressure engagement with base member 12.

With the embodiment of latch sub-assembly 56 illustrated in the drawings, opening 92 of sub-assembly 56 is formed by an upper, central portion of the back side of the cassette body 38; and lever 94 of the latch sub-assembly is pivotally supported by base member 12, in an upper, central front portion, thereof. Lever 94 has the shape of a backward L, including an upwardly extending leg 94a and a forwardly extending lower leg 94b, and the forward portion of the lower leg includes an upwardly extending front lip 94c. In the closed position of latch assembly 56, lower leg 94b of lever 94 extends through opening 92, and lip 94c of the lever engages a front surface of the back side of cassette body 36, tightly holding cassette 14 against base member 12.

Spring 96 is connected to lever 94 and urges that lever into a position in which the lever holds cassette 14 tightly against base member 12. To move latch assembly 56 to the open position, lever 94 is pivoted, counter clockwise as viewed in FIG. 6, and against the force of spring 96, moving lip 94c away from the edge of opening 92 and allowing the back side of cassette body 38—and thus the entire cassette 14—to pivot away from base member 12.

Apparatus 10 may be used for a variety of purposes and in a variety of specific applications. For example, apparatus 10 may be used during ophthalmic surgery to infuse and aspirate the surgical site. Even more specifically, apparatus 10 is very well suited for use in a modular console that includes a multitude of other modules for operating other instruments or for performing other tasks related to ophthalmic surgery. For example, apparatus 10 may be used in the console disclosed in copending application no. 330,926, the disclosure of which is herein incorporated by reference.

In such an application, apparatus 10 or the console may include a processor. The console processor, generally, may be used to control the overall operation of the console and to act as a communications interface between the console and the operator. Also, commands to operate various components of apparatus 10, including occlusion means 24, 110 and 112, may be generated by the console processor and transmitted to apparatus 10. In addition, data generated in or by apparatus 10 may be transmitted to the console processor to keep that processor, and the console operator, informed of that data.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed:

1. An infusion/aspiration apparatus comprising:
    a base member;
    a first cassette forming
        i) an aspiration passageway for receiving liquids and materials from a surgical site,
        ii) a collection area in fluid communication with the aspiration passageway for receiving and collecting said liquids and materials, and
        iii) a conduit in fluid communication with the aspiration passageway and the collection area for conducting said liquids and material from the aspiration passageway and into the collection area;
    means to selectively occlude said conduit to inhibit fluid flow therethrough;
    means releasably holding the first cassette on the base member;
    a second cassette including
        i) a body, and
        ii) an infusion tube connected to and supported by the body for conducting an infusion fluid; and
    means releasably holding the second cassette on the base member.

2. Apparatus according to claim 1, wherein:
    the base member and the second cassette form a vacuum passageway in fluid communication with the aspiration passageway to develop a vacuum pressure in the aspiration passageway; and
    the first cassettes includes a check valve disposed in the aspiration passageway to inhibit fluid flow through the aspiration passageway and into the vacuum passageway.

3. Apparatus according to claim 1, wherein:
    the first cassette includes
        i) a body forming the collection area and also forming front and back openings,
        ii) a T-tube having an upper, horizontal section and a vertical section;
    the upper section of the T-tube extends between the front and back openings of the cassette body and forms the aspiration passageway;
    the vertical section of the T-tube is connected to and is in fluid communication with said upper section, and forms said conduit.

4. Apparatus according to claim 1, wherein the occlusion means includes:
    a pincher block located adjacent said conduit, on a first side thereof;
    a pincher located adjacent said conduit, on a second side thereof, and supported for reciprocating movement; and
    means to reciprocate the pincher into engagement with the conduit to pinch the conduit between the pincher and the pincher block.

5. Apparatus according to claim 1, wherein the first cassette includes a check valve disposed in the aspiration passage to inhibit fluid flow through the aspiration passage and into the vacuum passageway.

6. Apparatus according to claim 1, wherein
    the means releasably holding the first cassette on the base member includes
        i) a pivot subassembly pivotally connecting the first cassette to the base member, and
        ii) a latch subassembly having a closed position and an open position;
    when the latch subassembly is in the closed position, the latch subassembly and the pivot subassembly hold the first cassette in a tight pressure engagement with the base member; and
    when the latch subassembly is in the open position, the latch subassembly allows the first cassette to pivot relative to the base member.

7. Apparatus according to claim 6, wherein:
    the latch subassembly includes
        i) an opening formed by the first cassette, and
        ii) a lever pivotally mounted on the base member; and
    when the latch subassembly is in the closed position, the lever extends through said opening and engages the first cassette to hold the main unit and the first cassette tightly together.

8. Apparatus according to claim 7, wherein the latch subassembly further includes a spring mounted on the base member and engaging the lever and urging the lever into engagement with the first cassette.

9. Apparatus according to claim 8, wherein:

the lever includes a upper leg, and a lower leg connected to the upper leg;

the lower leg includes a front, upwardly extending lip;

when the latch subassembly is in the closed position, said lip extends through said opening and extends forward of, and, is in pressure engagement with, a back side of the first cassette.

10. Apparatus according to claim 6, wherein:

the pivot subassembly includes
   i) a pair of pins mounted on the base member, and
   ii) a pair of hooks connected to the first cassette and extending outward therefrom; and
   each of the hooks is pivotally mounted on a respective one of the pins.

11. Apparatus according to claim 1, wherein:

the first cassette includes a body forming the liquid collection area and also a drain opening in fluid communication with the liquid collection area to drain liquids therefrom.

12. Apparatus according to claim 11, further comprising:

a drainage tube connected to the body of the first cassette, in fluid communication with the drain opening for conducting liquid therefrom; and means connected to the base member to selectively occlude the drainage tube to inhibit liquid flow therethrough.

13. Apparatus according to claim 12, wherein the means to selectively occlude the drainage tube includes:

a guide member mounted on the body of the first cassette and extending outward therefrom, wherein the drainage tube extends from the drainage opening, adjacent the guide member;

a pincher bar supported by the base member for reciprocating movement toward and away from the guide channel; and means connected to the pincher bar to move the pincher bar toward the guide member to pinch the drainage tube between the pincher bar and the guide member to inhibit liquid flow through the drainage tube.

14. An infusion/aspiration apparatus comprising:

a base member;

a first cassette releasably mounted to the base member, forming
   i) an aspiration passageway for receiving liquids and materials from a surgical site, and
   ii) a collection area in fluid communication with the aspiration passageway for receiving and collecting said liquids and materials;
   a second cassette releasably mounted to the base member, wherein the second cassette and first cassette are separately releasably mounted to the base member, including
   i) a body, and
   ii) an infusion tube connected to and supported by the body for conducting an infusion fluid.

15. Apparatus according to claim 14, wherein the base member includes a vacuum passageway and wherein the vacuum passageway is in fluid communication with the aspiration passageway of the first cassette to develop a vacuum pressure in the aspiration passageway when the first cassette is releasably mounted to the base member.

16. Apparatus according to claim 15, wherein:

the base member forms a cassette receiving slot extending through the base member vacuum passageway, wherein the slot separates the vacuum passageway, forming first and second sections of the vacuum passageway;

the second cassette further includes a vacuum passageway, wherein the vacuum passageway of the cassette body forms a third section of the vacuum passageway which is located in series between, and in fluid communication with, the first and second sections of the vacuum passageway, when the second cassette is releasably mounted in the cassette receiving slot.

17. Apparatus according to claim 16, wherein:

the second cassette has first and second sides, wherein the second cassette is releasably mounted to the base member by:
   i) a first flexible member mounted on the base member on the first side of the second cassette;
   ii) a second flexible member mounted on the base member, on the second side of the second cassette, and supported for reciprocating movement, and
   iii) means mounted on the base member to reciprocate the second flexible member into engagement with the second cassette and to force the second cassette into pressure engagement with and between the first and second flexible members.

18. Apparatus according to claim 17, wherein:

the first flexible member extends around the first section of the vacuum passageway and forms a seal between said first section and the second cassette; and the second flexible member extends around the second section of the vacuum passageway and forms a seal between said second passageway and the second cassette.

19. Apparatus according to claim 15, wherein the body of the second cassette includes:

first and second sections held together; and a filter captured between said first and second sections and extending across the vacuum passageway to inhibit the flow of liquid therethrough.

20. Apparatus according to claim 14, wherein:

the body of the second cassette has first and second opposite sections;

the first section of the second cassette forms a first recess providing access to the infusion tube;

the second section of the first cassette forms a second recess providing access to the infusion tube; and the means to selectively occlude the infusion tube includes:
   i) a pincher block mounted on the base member and aligned with the first recess,
   ii) a pincher supported by the base member for reciprocating movement into the second recess, and for reciprocating movement into the second recess; and
   iii) means to reciprocate the pincher into engagement with the infusion tube to pinch the infusion tube between the pincher block and the pincher.

21. Apparatus according to claim 14, wherein:

the body of the second cassette includes first and second sections held together;

the first section forms a first groove extending across the said first section;

the second section forms a second groove extending across the said second section;

the first and second grooves are aligned with each other and form a channel extending through the second cassette; and the infusion tube extends through said channel and is captured therein between the first and second sections of the body of the cassette.

22. Apparatus according to claim 14, wherein the base member defines a cassette receiving slot and the second cassette is disposed in the cassette receiving slot.

23. Apparatus according to claim 22, wherein the base member includes a base, and a top section having a C-shape and forming the cassette receiving slot.

24. Apparatus according to claim 14, further including means connected to the base member to selectively occlude the infusion tube to inhibit flow therethrough.

25. Apparatus according to claim 14, further including a means connected to the base member to selectively occlude the infusion tube to inhibit infusion therethrough.

26. An infusion/aspiration apparatus comprising:
a base member including a vacuum passageway;
a first cassette releasably mounted to the base member, forming:
   i) an aspiration passageway for receiving liquids and materials from a surgical site; and
   ii) a collection area in fluid communication with the aspiration passageway for receiving and collecting said liquids and materials;
a second cassette releasably mounted to the base member, wherein the second cassette and first cassette are separately releasably mounted to the base member, including:
   i) a body having first and second sections held together, and
   ii) an infusion tube captured between said first and second sections for conducting an infusion fluid;
   wherein the vacuum passageway of the base member is in fluid communication with the aspiration passageway of the first cassette to develop a vacuum pressure in the aspiration passageway when the first cassette is releasably mounted to the base member.

27. Apparatus according to claim 26, wherein:
the body further includes a filter captured between the first and second sections and extending across the vacuum passageway to inhibit the flow of liquid therethrough;
the first section of the body includes a first groove;
the first and second grooves are aligned with each other and form a channel extending through the body of the second cassette; and
the infusion tube extends through and is captured in said channel, between the first and second sections of said body.

28. Apparatus according the claim 27, wherein:
the means releasably holding the second cassette on the base member includes:
   i) a first flexible member mounted on the base member on a first side of the second cassette;
   ii) a second flexible member mounted on the base member mounted on the base member on a second side of the second cassette; and
   iii) means mounted on the base member to reciprocate the second flexible member into pressure engagement with the second cassette to hold the second cassette in pressure engagement between the first and second flexible members;

the first section of the second cassette forms a first recess providing access to the infusion tube;
the second section of the second cassette forms a second recess providing access to the infusion tube; and
the means to selectively occlude the infusion tube includes:
   i) a pincher block mounted on the base member and aligned with the first recess,
   ii) a pincher supported by the base member for reciprocating movement into the second recess, and
   iii) means to reciprocate the pincher into engagement with the infusion tube to pinch the infusion tube between the pincher block and the pincher.

29. Apparatus according to claim 28, wherein the first flexible member extends around the vacuum passageway and forms a seal between the vacuum passageway and the first section of the second cassette; and
the second flexible member extends around the vacuum passageway and forms a seal between the vacuum passageway and the second section of the second cassette.

30. An infusion/aspiration apparatus comprising:
a base member including a vacuum passageway and a slot extending through the vacuum passageway, wherein the slot separates the vacuum passageway in the base member, forming a first and second sections of the vacuum passageway;
a first cassette releasably mounted to the base member, forming
   i) an aspiration passageway for receiving liquids and materials from a surgical site, and
   ii) a collection area in fluid communication with the aspiration passageway for receiving and collecting said liquids and materials;
a second cassette releasably mounted to the base member, wherein the second cassette and first cassette are separately releasably mounted to the base member, including
   i) a body having a vacuum passageway therethrough, wherein the vacuum passageway of the cassette body forms a third section of the vacuum passageway located in series between, and in fluid communication with, the first and second sections of the vacuum passageway, when the second cassette is positioned in the cassette receiving slot;
   ii) an infusion tube connected to and supported by the body for conducting an infusion liquid;
   wherein when the second cassette is releasably mounted in the receiving slot, the first, second, and third sections of the vacuum passageway are in fluid communication with the aspiration passageway of the first cassette to develop a vacuum pressure in the aspiration passageway when the first cassette is releasably mounted to the base member.

\* \* \* \* \*